United States Patent [19]

Beinsen et al.

[11] 4,059,113

[45] Nov. 22, 1977

[54] ASPIRATORS FOR MEDICAL PURPOSES

[76] Inventors: Dieter Beinsen, Geschw. Schollstr. 12, Salzgitter 1; Otto Kribitzneck, Dierkinkstr. 14, Walsrode, both of Germany

[21] Appl. No.: 617,915

[22] Filed: Sept. 29, 1975

[30] Foreign Application Priority Data

Nov. 23, 1974 Germany .............................. 2456067
Sept. 28, 1974 Germany .............................. 2446470

[51] Int. Cl.² .................... A61L 1/00; A61M 1/00; B65B 31/04; B65D 51/16
[52] U.S. Cl. ............................ 128/276; 21/56; 53/21 FC; 53/22 R; 53/86; 137/205; 137/241; 215/309; 220/204
[58] Field of Search ............... 128/276, 278; 21/56, 21/104, 91, 94; 137/205, 241; 220/203, 204, 303; 215/307, 309, 315, 260; 206/808

[56] References Cited

U.S. PATENT DOCUMENTS

| 3,486,840 | 12/1969 | Burton et al. ........................ 21/56 |
| 3,773,211 | 11/1973 | Bridgman ....................... 128/276 X |
| 3,805,788 | 4/1974 | Kleiner ................................ 128/276 |
| 3,833,000 | 9/1974 | Bridgman ........................... 128/276 |
| 3,855,997 | 12/1974 | Sauer ............................ 128/276 X |

*Primary Examiner*—Joseph Scovronek
*Attorney, Agent, or Firm*—Salter & Michaelson

[57] ABSTRACT

Vacuum aspirator for medical use of the kind which is required to be sterilized by steam and then evacuated so as to be ready for use. Object of the invention is to provide an aspirator which is suitable for repeated use and re-sterilization. The aspirator is provided with an outwardly-opening, non-return valve which may be in a closure plug of a flask of the aspirator or mounted at or inserted in the end of a suction connection remote from the flask of the aspirator.

6 Claims, 12 Drawing Figures

U.S. Patent  Nov. 22, 1977  Sheet 1 of 4  4,059,113
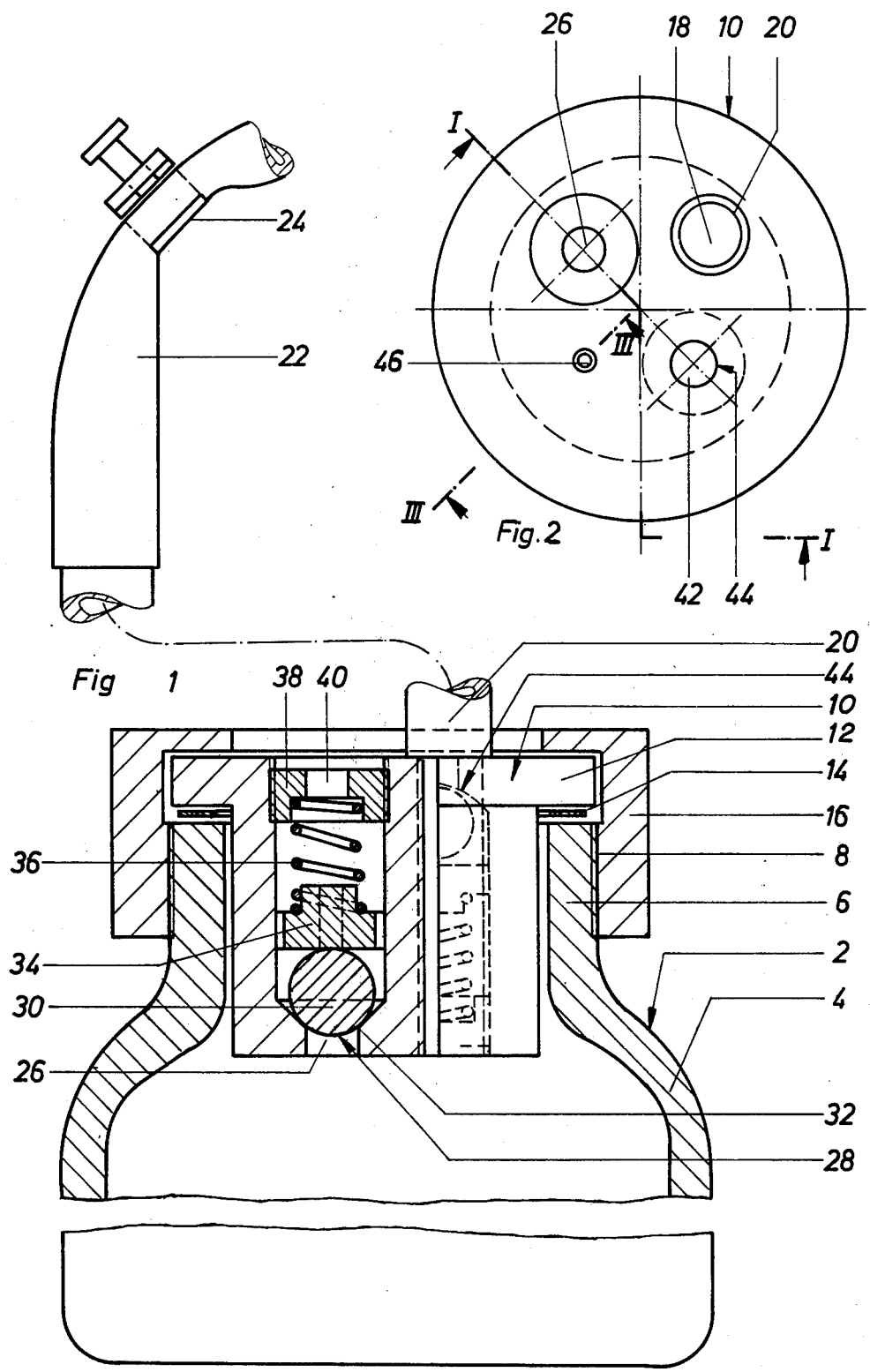

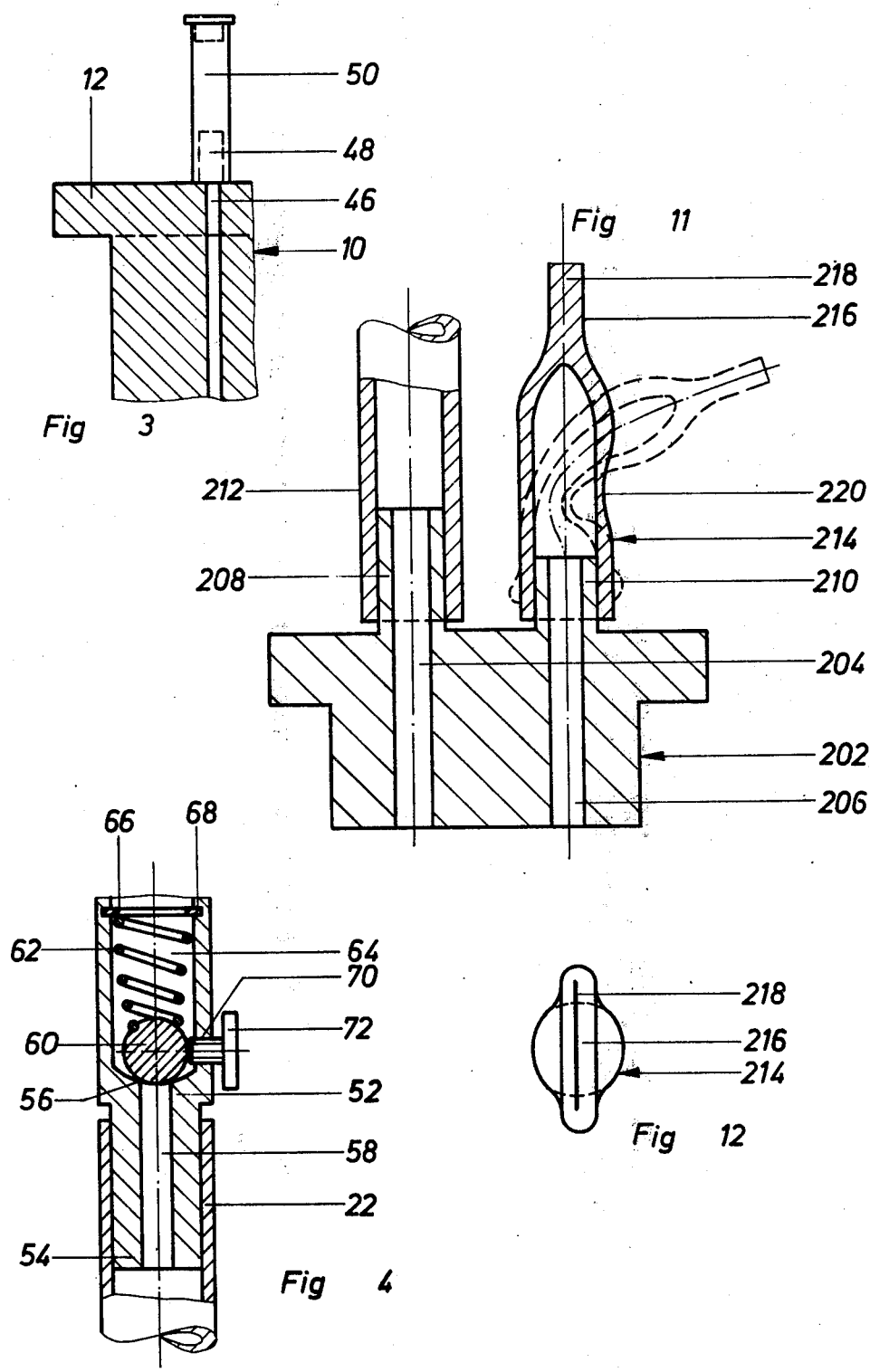

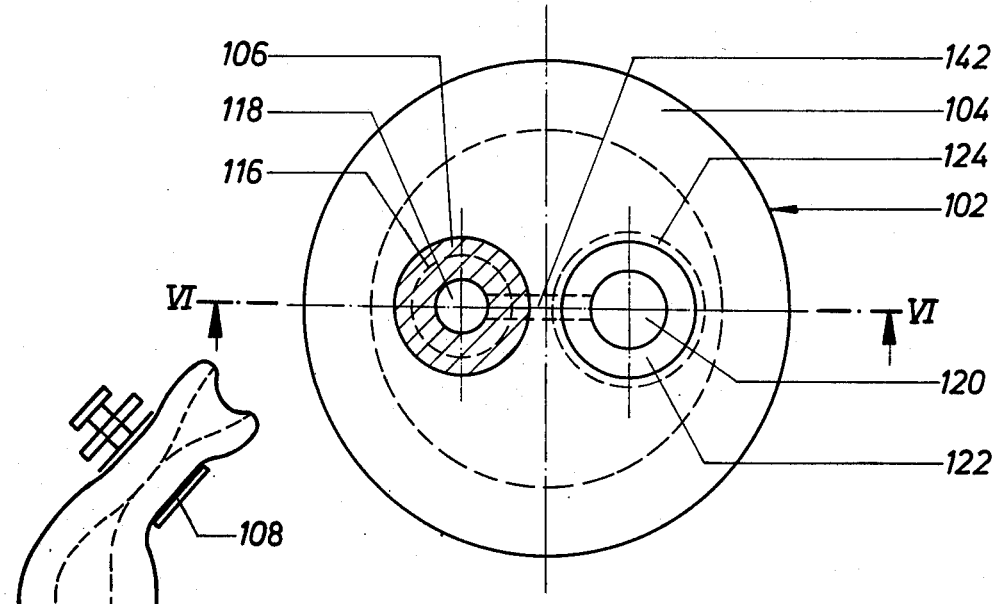
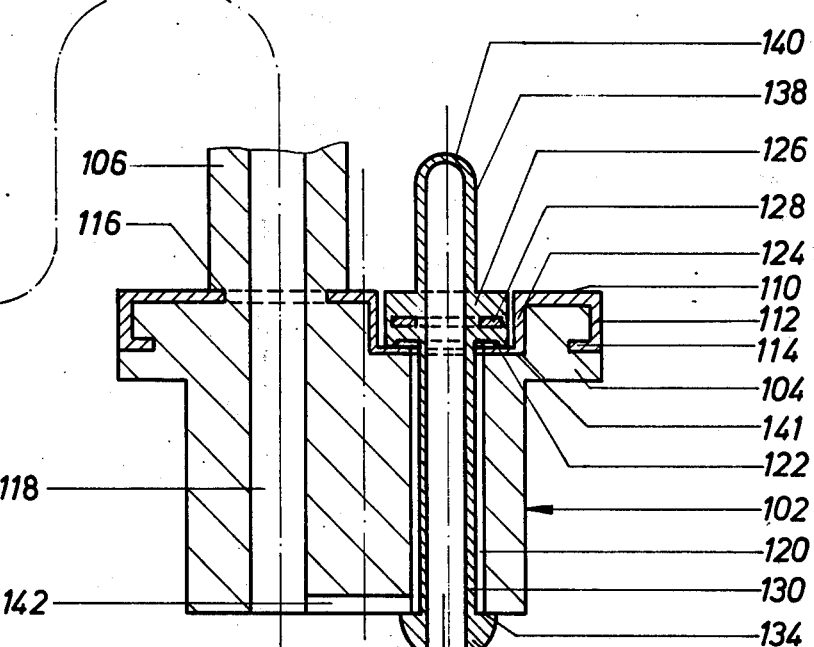

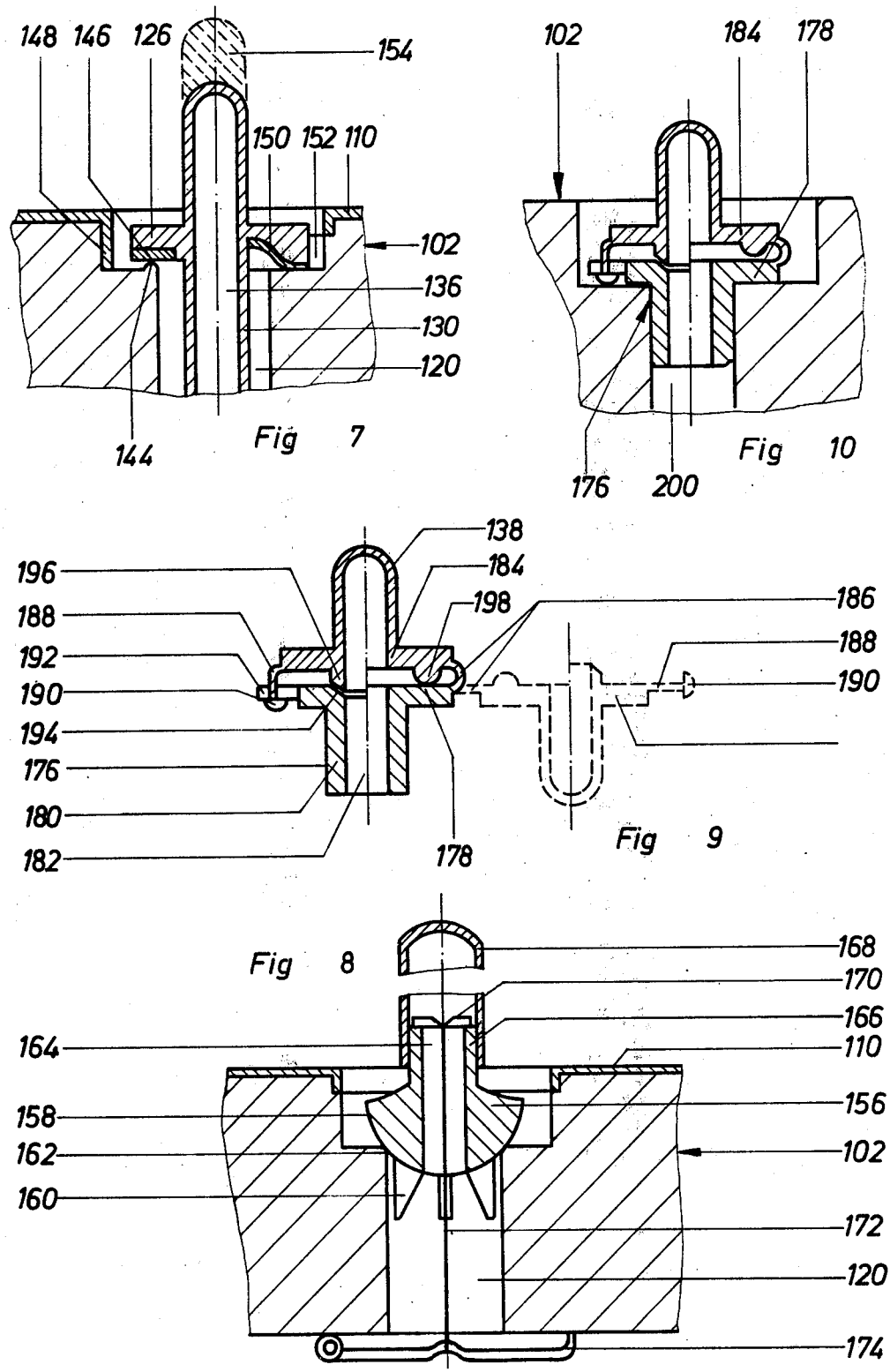

ASPIRATORS FOR MEDICAL PURPOSES

The invention concerns a method for the evacuation of aspirators to be used for medical purposes and an aspirator for carrying out the method. Aspirators are used in medicine to extract secretions from body cavities and also as receiving vessels when taking blood from donors.

Known aspirators comprise flasks provided with closure plugs having thereon a connecting piece onto which a connecting tube is pushed. The closed flasks are sterilised in a steriliser and are then evacuated by means of a vacuum pump. The connecting tube is then pinched by a tube clamp so that the vacuum is maintained. The flasks are then put into sterile bags until they are to be used. As well as the fact that evacuation of the flasks entails an additional working step, there is also a danger of re-infection of the connecting end of the connecting tube during this process.

Aspirators are also known which are designed as disposable or throw-away flasks made of synthetic plastics material and sterilised by gamma rays, but disposable aspirators of this type are expensive.

It is an object of the invention to develop a method for the evacuation of aspirators which is suitable for repeated application, which is easier to carry out than the known method described above and in which the danger of re-infection is considerably decreased.

This object is solved according to the invention in that an aspirator, which is provided with an outwardly-opening non-return valve, is subjected to vacuum in a sterilisation apparatus after being sterilised therein by the application of steam. The non-return valve may be mounted in the closure plug of the aspirator. It is also possible to mount the non-return valve at the free end of a suction connection of the aspirator and, in particular, to insert it removably within the free end of the suction connection.

In order to bring about the equalisation of pressure in the high pressure steam inside and outside the aspirator there may be additionally provided an aperture closed by a spring-loaded valve which opens towards the interior of the aspirator.

In a vacuum aspirator for carrying out the method as set out hereinbefore, an outwardly-opening non-return valve may be provided in the closure plug of the flask. An inwardly-opening valve may also be provided in the closure plug, where necessary. In another embodiment of a vacuum aspirator an outwardly-opening non-return valve attachable to the suction connection of the flask plug is provided and may be supplemented by a spring-loaded valve opening inwardly.

In a non-return valve for an aspirator which is simple in design and assembly and which can be easily connected to and disconnected from an aspirator and, in particular to a plug therefor, even by inexperienced personnel, the valve closure member of the non-return valve has a tension loaded spring element.

The valve closure element may be formed from a soft elastic material and may be of unitary construction having an extension led through the valve bore of the valve seating body. It is convenient in this case to provide an abutment at the free end of the extension which can be engaged with a shoulder of the valve seating body, the distance between the valve seating and the shoulder being equal to or smaller than the distance between the seating surface of the valve closure member and the abutment.

A resilient band may also be provided as the spring element being attached at one end to the valve closure body and at the other end of the valve seating body.

A valve closure element made from a soft elastic material may be strengthened by means of a rigid body. Thus for example an annular disc acting as the seating surface of the valve closure member may be provided as a strengthening.

The design of the aspirator may be further simplified in that the valve closure member has a hollow body on its upper side acting as a vacuum indicator which is connected to the vacuum side of the valve member through a port in the valve closure member and which either changes its length characteristically or becomes kinked when a vacuum is present in the flask. With a valve closure member made from a soft elastic material the hollow body acting as the vacuum indicator may be formed integrally with the valve closure member, thus considerably simplifying manufacture.

The valve closure member may however also be designed to be rigid, in which case a nipple can be provided on its upper side which is connected to the vacuum side of the valve closure member, the elastic hollow body acting as the vacuum indicator being mounted on the nipple in seal-tight manner.

Preferably, according to the invention, the valve seating and the valve bore are formed in the closure plug of the aspirator.

The closure plug of the aspirator may be formed from a soft elastic material and may be strengthened by means of a rigid body essentially of plate form, which, for example, may be formed on the upper side of the closure plug and which may overlap the edge of the valve closure body at the outside. The plate may also be provided with flanges which for example may form the surrounding wall of a recess, in whole or in part, in which the valve seat is formed at a distance from the upper side of the closure plug.

In another form of embodiment in which the valve closure body made from a soft elastic material is integral which the hollow body which acts as the vacuum indicator, the valve closure member may be provided on the sealing side with a multiplicity of integral projections around its circumference, by means of which the valve closure member is connected to the valve seating body. In this case the valve closure body may be integral with the valve seating body, the two bodies being connected by at least one of the projections.

At least one of the projections of the valve closure body should in this case form a self-locking overlap of the valve seating body.

In a convenient form the projection which connects the valve seating body with the valve closure body forms a connection of a hinge type, while the other projection is firmly connected as a shackle to one of the bodies, the said shackle being releasably connected to the other body by means of a locking element.

In non-return valves of the last-mentioned type the valve seating body may be provided with a nipple type projection, by means of which it can be tightly inserted into a bore in the closure plug or into a tubular housing connected to the suction tube.

In another form of embodiment the non-return valve is formed as a tubular body one end of which can be fitted on to a connecting nipple, for example, on the closure plug of the flask while it is provided at its other end with a lip-shaped sealing section. The tubular body may also be provided on the vacuum side of the sealing section and may have a kinking position effective under the influence of vacuum in such a way that when the non-return valve is bent over this indicates that the flask contains a vacuum.

The flask plug may alternatively have a connection for an elastic vacuum indicator.

By way of example, several forms of aspirator in accordance with the invention are now described in detail with reference to the drawings, in which:

FIG. 1 shows a side view of an aspirator, the upper part being sectioned along the line I—I in FIG. 2;

FIG. 2 is a plan view of the closure plug of the aspirator shown in FIG. 1;

FIG. 3 is a section along the line III—III in FIG. 2;

FIG. 4 is a longitudinal section of a non-return valve which can be slipped on to the end of a connecting tube shown in FIG. 1;

FIG. 5 is a plan view of a closure plug for another form of aspirator with a built-in non-return valve;

FIG. 6 is a section along a line VI—VI in FIG. 5;

FIG. 7 shows alternate forms of a valve closure member for the closure plug of FIG. 6;

FIG. 8 shows in section another form of a non-return valve according to the invention;

FIG. 9 shows in section yet another form of a non-return valve;

FIG. 10 shows the non-return valve of FIG. 9 connected to a closure plug for the aspirator;

FIG. 11 shows another form of a non-return valve connected to a closure plug, and FIG. 12 shows a plan view of the non-return valve shown in FIG. 11.

The vacuum aspirator 2 illustrated in FIG. 1 has a known flask body 4 made of glass, the neck 6 of which has an external thread 8. A closure plug 10 is inserted in the neck of the flask and its flange 12 is applied against the front face of the neck of the flask. A seal 14 is arranged between the flange 12 and the top face of the neck of the flask. The flask plug 10 is held in position by a screw cap 16.

The flask plug 10 has a bore 18 (see FIG. 2) which is connected to a connecting piece 20 on the upper side of the plug onto which the connecting tube 22 can be attached in a known manner, said tube being capable of being pinched by a tube clamp 24.

Another opening 26 is provided in the flask plug and can be closed by a non-return valve 28, opening outward. The non-return valve 28 has a valve ball 30 acting in conjunction with a valve seating 32. The valve ball 30 is loaded through a spring biased washer 34 by a compression spring 36 the other end of which is applied against a spring biased washer 38, which is here designed as an insulator bolt with a central bore 40. The spring washer 34 has notches parallel to its axis around its circumference which ensure connection between the upper and lower sides of the spring washer. One of the valve elements 30 and 32 has a yielding surface. It is, for example, possible to use a rubber valve ball and a rigid valve seating or, alternatively, a metal ball acting in conjunction with a yielding seating such as, for example, an O-ring spring-loaded in a groove in the plug. Flat seals are, of course, also possible, for example a flat seal on the underside of the spring washer 34. The spring 36 is so dimensioned that the valve opens when the flask is within an evacuated space.

As well as the opening 26, an additional opening 42 (see FIG. 2) is provided which has a valve 44 opening into the interior of the flask. The valve 44 may be assembled from the same basic constructional parts as the valve 28. The spring of the valve 44 is so dimensioned that the opening 42 in the flask is securely sealed by the valve closure member in vacuum. Additionally, the valve must open when an overpressure is applied in the steam steriliser.

The plug is finally provided with another opening 46 (see FIGS. 2 and 3) which opens on the upper side of the plug 10 within a connecting piece 48 onto which there can be slipped a vacuum indicator 50 which either decreases in height or bends over when a vacuum is present. (see FIG. 3).

The vacuum aspirator described is placed in the closed state and with the connecting tube 22 closed in a pressure steriliser. During a high pressure stage of the steriliser it is possible for steam to enter the vacuum aspirator through a valve, when such a valve is provided. During the vacuum phase of the steriliser, air and any steam which has entered is pumped out through the valve 28. After completion of the vacuum phase the interior of the vacuum aspirator is therefore at the highest vacuum attained in the steriliser. The sterilised and evacuated flask is then removed from the steriliser and can immediately be packed in sterile conditions in a known manner and brought into use. It is thus unnecessary to attach the sterilised flask to a vacuum pump with the ensuing danger of infection of the open end of the tube 22.

In the second embodiment, an outwardly-opening non-return valve is provided at the end of the connecting tube 22 of the vacuum aspirator. Such an arrangement is illustrated in FIG. 4.

Referring to FIG. 4, a valve body 52 is inserted in the end of the connecting tube 22 by means of a connecting piece 54 which may have circumferential corrugations on its exterior, in a known manner, to increase the sealing effect. A valve seat 56 is provided in the valve body 52 at the end of a bore 58 leading through the connecting piece 54. The valve closure member is a ball 60 which is loaded by the pressure of a spring 62. The spring 62 is formed in this case as a conical spring which is applied against the ball, with the end of smaller diameter of the spring slightly overlapping the ball 60. The diameter of the opposite end of the spring 62 corresponds to the diameter of the bore 64 of the valve body 52. The spring 62 is here supported against a spring ring 66, which is snapped into a groove 68 in the upper end of the valve body 52. In this manner a very simple valve construction with few components is achieved. Evacuation of the flask, when in the steriliser, takes place through the non-return valve inserted in the end of the tube 22. After removal of the vacuum aspirator from the steriliser, the non-return valve can remain in the tube 22. Before packing or bringing the aspirator into use, a pinching clamp is placed on the connecting tube 22. The non-return valve is then removed from the tube 22 only when the aspirator is brought into use. In this way the sterility of the connecting tube 22 over its whole length up to the connection to the suction tube is ensured. A non-return valve of the type illustrated in FIG. 4 can easily be manufactured as a cheap mass production article, for example from synthetic material. In this connection it is not entirely forbidden on technical grounds to subject the non-return valve shown in FIG.

4 to re-sterilisation and evacuation with the flask. A recycling of the valve is an obvious possibility.

Insofar as a steam inlet valve can be dispensed with in this embodiment, it is possible to use a simple flask plug which carries only the connecting piece 20 for the connecting tube 22 and a connecting piece for the vacuum indicator.

In the non-return valve illustrated in FIG. 4, the valve housing 52 can be provided, in addition, with a device to lift the ball 60 away from the valve seating 56. For example, the housing may be provided with a thread 70 at the level of the ball 60 into which a screw 72 is screwed, by means of which the ball 60 can be pushed to one side in its valve seat 56, in order to open the valve. In this case, it is necessary to lengthen the valve housing 52 above the spring ring 66 and to provide it with a tube connection. In such an embodiment a tube clamp can be dispensed with. It is possible to adjust the valve opening very exactly by means of the screw 72.

Insofar as a steam entry valve may also be required in the embodiment according to FIG. 4, this may be arranged in one valve body together with the outwardly-opening non-return valve. Both valves then open into a common tube connection. It would also be possible to mount the two valves in separate housings which could be joined by means of T- or Y-shaped connecting pieces, the third arm of which forms the tube connection.

It is also possible to provide a T-shaped connecting piece, one arm of which can be attached directly to the connecting piece 20 of the flask plug while the outwardly-opening non-return valve is arranged on another arm. The third arm then forms the connecting piece for the tube. If a steam entry valve is also necessary in this embodiment a connecting piece in the form of a cross may be used.

In the form of embodiment according to FIGS. 5 and 6 a closure plug 102 is provided which has a circumferential application and sealing rim 104 and which is of one piece construction with a connecting tube 106 which for its part can be tightly closed by means of a pinching clamp 108. The closure plug 102 may for example consist of a soft elastic material, particularly a heat resistant rubber. In order to give increased stiffness to the closure stopper, a rigid plate 110 is provided on its upper side, in particular a metal plate of rust resistant material. In this example, the plate has a circumferential rim 112 with an inwardly directed flange 114 at its free end. The plate 110 has a bore 116 through which is led the tube bore 118. The bore 116 is somewhat smaller than the external cross-section of the tube connection 106, in order to bring about increased stiffness and in particular to prevent deformation by the pressure of the atmosphere which acts on the upper side of the plug in vacuum. The plug 102 is further provided with a bore 120 which serves as the valve bore and which is in connection at its end with a valve seating 122 sunk into the upper side of the closure plug. The valve seating and the recess are here formed by a deep-drawn section 124 of the plate 110. In the recess thus formed, there lies a valve closure member 126, made from a soft elastic material which may be stiffened for example by means of a metal ring 128. The valve closure member 126 leads on its under side into a body 130 of tubular form the external diameter of which is smaller than the internal diameter of the valve bore 120. At the lower end of the tubular body a bulge 132 having an abutment surface 134 is formed. The internal bore 136 of the tubular body 130 continues upwards through the valve closure member 126 and leads into a cylindrical hollow body 138 on the upper side of the valve closure member 126 with a dome-shaped closure 140.

A circumferential sealing bulge 144 may be provided on the underside of the valve closure member 126.

The distance between the valve seating 122 and the underside of the plug 102 is equal to or greater than the distance between the sealing underside of the valve closure member 126 and the abutment surface 134 of the bulge 132. The valve closure member described is introduced with the bulge 132 into the valve bore 120 from above until the bulge 132 on the underside of the plug comes into abutment with the corner 134. The valve closure member then lies without play, preferably under slight prestress, on the valve seating. The prestress is here provided by the elasticity of the tubular body 130.

On the underside of the plug 102, a recess 142 is provided which opens into the valve bore 120. The underside of the plug 102 and thus the interior of an aspirator closed by the plug are thereby connected to the valve seating through the recess 132 and the valve bore 120. If the aspirator is then exposed to an external vacuum in a steriliser the valve closure member 126 is lifted off and the air contained in the flask can be pumped out. As soon as the internal vacuum corresponds to the external vacuum, the valve closure member is again applied to the valve seating. If the vacuum in the steriliser is then removed the valve closure member is pressed with a tight seal against the valve seating by the external pressure and the vacuum in the flask is thus maintained. At the same time the hollow body 138 is compressed by the external pressure so that it kinks or is changed in its length. In a modification of the example of embodiment illustrated, the hollow body 138 may for example be designed in concertina fashion so that it is compressed in length. There may however also be provided a safety kinking position, for example, by means of weakening at one position in the wall which leads to a kinking due to the external pressure.

The valve closure member 126 can be readily manufactured as a one piece body by vulcanisation of a rubber composition. The valve closure body could therefore by provided as a disposable element where the valve closure member is removed from the valve bore 120 when cleaning the flask after use. Only the smooth bore then requires to be cleaned. A fresh valve body can easily be inserted subsequently even by untrained personnel.

It is not necessary to provide the recess 142. For example, the bulge 132 could also be provided with connecting grooves or the tubular section 130 could have perforations through which connection to the interior is made.

FIG. 7 shows modifications to the embodiment of the valve closure body shown in FIG. 6. On the left-hand side the valve seat has a sealing bulge 144 and a metal disc 146 of rust resistant material is vulcanised onto the underside of the valve closure body thus providing a hard and smooth sealing surface while at the same time stiffening the valve closure member. On the left-hand side the plate 110 has a cylindrical rim on the inner side. The modification on the right-hand side, instead of the plane disc 146 of the embodiment on the left, includes a shaped disc 150 arranged on the underside of the valve closure member 126, the outer edge of said disc forming the sealing surface acting in conjunction with the valve seat 152 which is plane in this case. Shown in dotted lines at the upper extremity of the hollow body 138 is a dome of greater mass 154 which acts as a weight by means of which the kinking of the hollow body 138 to indicate a vacuum is ensured.

In the embodiment according to FIG. 8, which is a further modification of FIG. 6, a body 156 made from a rigid material is provided as the valve closure member and has a spherical surface 158 on its underside, Guide projections 160 are provided on the underside of the body 156 by means of which the body 156 is guided within the valve bore 120. The valve seating itself is formed in this case by a chamfer 162 at the upper end of the valve bore 120. The valve closure body 156 has a bore 164 and a nipple 166 at its upper end on to which a hollow body 168 serving as a vacuum indicator can be pushed with a tight seal. In the upper face of the nipple 166, a wire strap 170 is inserted over which a rubber band 172 is led. The rubber band 172 passes through the bore 164 and the valve bore 120 to the underside of the plug 102 and is there, for example, secured on to a rotatable wire strap 174. The pre-stress on the valve closure body is provided by the rubber band 172 and in other respects this valve operates as described with reference to FIG. 6.

In the embodiment according to FIG. 9, a valve seating body 176 is provided with a seating plate 178 and a nipple 180 arranged on its underside, with a valve bore 182 passing through them. A plate-shaped valve closure member 184 is connected to the valve seating plate 178 by at least one hinge shackle 186. A closure shackle 188 is provided on the valve closure member 184 for the hinge shackle 186, where said closure shackle has a knob type abutment 190 at its end. The valve seating plate has a notch 192 in this region in which the closure shackle 188 can be engaged. The valve closure body 184 again is provided with a bore and a hollow body 138 acting as a vacuum indicator, as in the embodiments described in FIGS. 6 to 8. In the form of embodiment illustrated on the left in FIG. 9, a frusto-conical valve seat 194 is provided which acts in conjunction with a sealing ring 196 on the underside of the valve closure member, which can be provided with a corresponding chamfer. In the embodiment illustrated on the right of the centre line in FIG. 9, an annular sealing bulge 198 is provided. In FIG. 9, the valve closure member 184 is illustrated in its opened position in dotted lines on the right. As can be seen from this, the whole valve can be manufactured in a simple form which is easy to insert. The hinge shackle 186 and the closure shackle 188 should be so dimensioned that the sealing elements are applied to each other with slight pre-stressing after engagement of the closure shackle. As is illustrated in FIG. 10, the valve closure element according to FIG. 9 with its nipple 180 is inserted in a tight manner in a bore 200 of a closure plug 102. The pre-stressing of the nipple 180 in the bore 200 must be rather greater than the pre-stressing of the valve closure body in order to prevent the valve from being drawn out of the bore 200 under vacuum. If these conditions are provided, the valve will be lifted under vacuum against the pre-stressing by the shackles 186 and 188 until the same vacuum is produced inside and outside the valve. The non-return valve according to FIGS. 9 and 10 can be easily and simply manufactured to be disposable after use.

In the foregoing, the embodiments of the valve described are built into a closure plug of an aspirator. It is obviously also possible to design the valve seat and valve bore in a separate tubular valve housing which then, for example as described above with reference to FIG. 4, can be inserted into the end of the connecting tube 106. It is also not essential to arrange for the valve seating to be sunk. The sunk arrangement has the advantage that the valve is protected against accidental contacts. A final embodiment is illustrated in FIGS. 11 and 12. Here the closure plug 202 which has two parallel bores 204, 206 has two connecting nipples 208, 210 on its upper side. The plug 202 may be example be formed from a rigid heat resistant material, for example Makralon, and in order to reduce material usage it may have recesses on the underside by means of which a uniform distribution of material favourable to injection moulding is achieved. A connecting tube 212 which corresponds to the connecting tube 106 of FIG. 6 is slipped on to the nipple 208. A tubular body 214 flattened at its upper end 216 is slipped onto the connecting nipple 210. At this end a lip-shaped seal with a slit-shaped sealing cross-section 218 is provided. The lips normally lie against each other with slight pre-stressing, where this pre-stressing may for example be produced by means of clamping ribs provided on the external side. The lip seal opens as soon as the internal pressure is greater than the external pressure. Thus the air in the flask can escape under external vacuum conditions. After evacuation the lips of the lip seal are pressed closely together by the pressure of the atmosphere. The casing of the valve body 214 has a safety kinking position 220 on its right-hand side formed by a wall region of reduced thickness. Under atmospheric pressure this position deforms inwardly so that the tubular valve 214 kinks over into the position illustrated in dotted lines so that a vacuum indicator is simultaneously provided. This form of embodiment provides a non-return valve which is particularly simple to manufacture.

In the embodiment shown in FIGS. 11 and 12, it is obviously also possible to arrange the connecting nipples to be sunk into the upper side of the closure plug 202. The tubular valve body 214 may once again be provided with a circumferential bulge at its attachment end in order to increase the pre-stressing. Pre-stressing of the sealing lips can at the same time be increased by means of prevulcanised bulges. It is also possible to superimpose a hairpin spring in order to achieve the sealing pre-stress.

A lip seal can also be provided in or on the connecting tube of the aspirator as a non-return valve. This tube may for example be formed as a corresponding moulded body which may for example be provided with a flattened section in which the walls lie against each other. A lip valve is also achieved in this manner where it is again possible to provide a safety kinking position. When the lip seal is arranged in or on the connecting tube, a section should be provided at the end of the tube into which the draining tube to be attached can be inserted without opening the non-return valve. The arrangement can be so designed in this manner that the drainage tubes open the lip seal simultaneously when it is inserted.

It is also possible to slip a non-return valve according to FIG. 11 on to a nipple by means of its lower end and to insert the nipple in the outer end of the connecting tube of the aspirator.

As a supplement, it should be pointed out with reference to the form of embodiment of FIG. 5 that projections extending parallel to the axis can be provided on the valve closure member, said projections having hook shaped bends by means of which they engage under the valve seating plate. A projection of this kind could in this case extend over a considerable part of the circumference. The valve seating body and the valve closure member would then form two separate parts.

What we claim as our invention and desire to secure by Letters Patent of the United States is:

1. A vacuum aspirator for removing fluids from body cavities comprising a container for receipt of such fluids, a closure for closing said container, means supported by said closure for receiving and thereafter directing said fluids through said closure into said container, combined valve means operatively associated with said closure for sequentially admitting pressurized steam to interior portions of said container and thereafter evacuating the same, said valve means including a first one-way inwardly opening inlet valve portion normally biased in a closed position to admit steam above a predetermined relative pressure therepast and a second one-way outwardly opening outlet valve portion normally biased in a closed position to permit the passage of gas within said container outwardly thereof during evacuation of said container, said receiving means and said valve means operable to maintain said container under vacuum until use of said aspirator.

2. Apparatus according to claim 1, in which the one way outlet valve is positioned in a tube which is connected to the container.

3. Apparatus according to claim 2, in which the one-way outlet valve has a cylindrical housing having a connection piece inserted into the end of the connecting tube, the housing having a conical valve seating therein, and a valve closure member in the form of a ball loaded by means of a conical spring against the seating, the larger diameter end of the spring engaging against the end of the valve body remote from the valve seating.

4. The aspirator construction of claim 1, said inlet and outlet valve portions being separate valve members.

5. The aspirator construction of claim 4, wherein such separate valve members are positioned within said closure.

6. The aspirator construction of claim 4, including tube means, one of said valve members positioned to close said tube means, said tube means in turn connected to said receiving means.

* * * * *